(12) United States Patent
Sunde et al.

(10) Patent No.: US 6,343,226 B1
(45) Date of Patent: Jan. 29, 2002

(54) MULTIFUNCTION ELECTRODE FOR NEURAL TISSUE STIMULATION

(75) Inventors: Niels Sunde, Risskov; Jens Chr. Sørensen, Egå, both of (DK)

(73) Assignee: NeuroKinetic ApS, Aarthus C (DK)

( * ) Notice: Subject to any disclaimer, the term of this patent is extended or adjusted under 35 U.S.C. 154(b) by 0 days.

(21) Appl. No.: 09/409,458

(22) Filed: Sep. 30, 1999

(30) Foreign Application Priority Data

Jun. 25, 1999 (DK) .......................................... 1999 00919
Aug. 30, 1999 (EP) ............................................ 99202787

(51) Int. Cl.⁷ ................................................. A61N 1/05
(52) U.S. Cl. ...................... 600/378; 607/116; 607/544; 606/129
(58) Field of Search ................................. 600/373, 378, 600/372, 590; 607/116–118; 606/129, 130

(56) References Cited

U.S. PATENT DOCUMENTS

| | | | |
|---|---|---|---|
| 4,245,645 A | | 1/1981 | Arseneault et al. |
| 4,903,702 A | | 2/1990 | Putz |
| 5,676,655 A | | 10/1997 | Howard, III et al. |
| 5,788,713 A | * | 8/1998 | Dubach et al. ............. 606/130 |
| 5,843,148 A | * | 12/1998 | Gijsbers et al. ............. 607/116 |
| 5,928,143 A | * | 7/1999 | McNaughton ............... 600/373 |
| 6,011,996 A | * | 1/2000 | Gielen et al. ............... 607/116 |
| 6,094,598 A | * | 7/2000 | Elsberry et al. ............. 607/116 |
| 6,171,239 B1 | * | 1/2001 | Humphrey .................. 600/372 |

FOREIGN PATENT DOCUMENTS

| | | |
|---|---|---|
| EP | 0 183 605 | 6/1986 |
| EP | 0 319 844 | 6/1989 |
| WO | WO 97/10784 | 3/1997 |

* cited by examiner

*Primary Examiner*—Linda C. M. Dvorak
*Assistant Examiner*—David Ruddy
(74) *Attorney, Agent, or Firm*—Merchant & Gould P.C.

(57) ABSTRACT

Techniques whereby electrical stimulation to treat symptoms from central and peripheral nervous system disorders such as those found in e.g. Parkinson's disease, epilepsy, psychiatric illness and intractable pain, using a quadripolar deep brain stimulation electrode connected to an implantable pulse generator have been expanded. By an implantation of an electrode, it is important for the outcome to determine the optimal placement of the electrode. By the invention, an electrode device is provided allowing stimulation of a large volume of neural tissue in combination with simultaneous microelectrode recording. Other improvements involve a temporary electro-physiological microrecording microelectrode/stilette 1, a bent electrode tip, a split electrode tip or an asymmetrical electrical stimulation field. This technique allows for a less traumatic localisation of the optimal neural stimulation area by microelectrode recording in combination with the placement of the permanent deep brain stimulation electrode.

21 Claims, 2 Drawing Sheets

Figure 3:
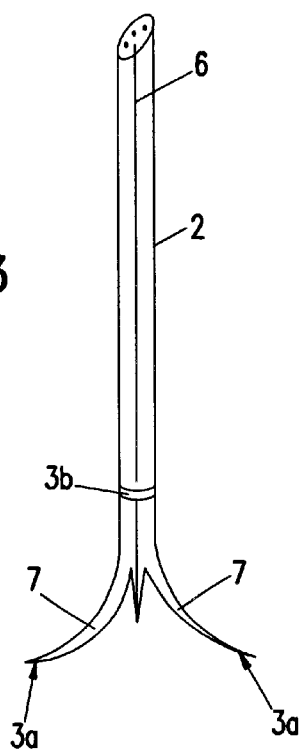

FIG. 1
FIG. 2
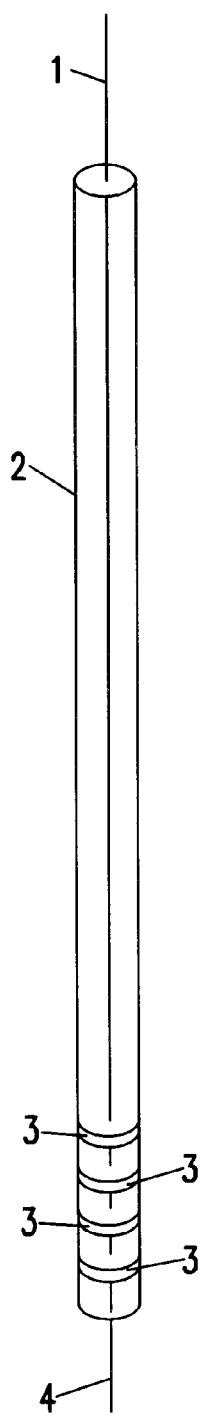
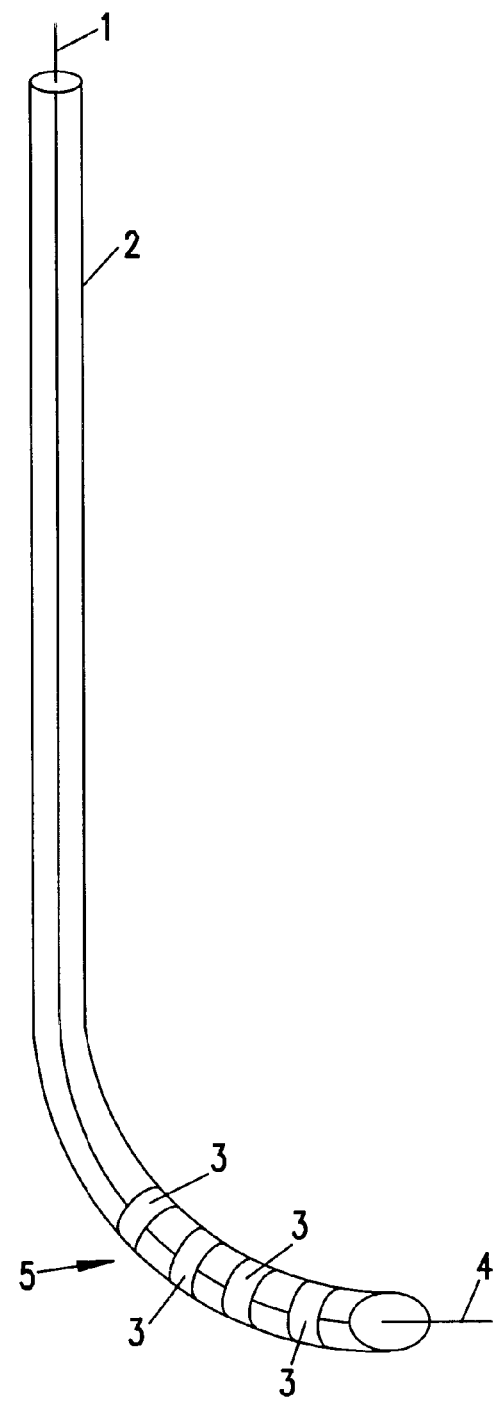

MULTIFUNCTION ELECTRODE FOR NEURAL TISSUE STIMULATION

The invention relates to the electrical stimulation of neural tissue in order to abolish the symptoms of nervous system and neuromuscular disorders.

So far electrical treatment with deep brain stimulation (DBS) has primarily been used to treat symptoms of Parkinson's disease which is a disorder affecting the nerve cells in the brain stem. These cells contain the nerve-transmitter dopamine. The disabling symptoms of the disease are tremor, muscular rigidity and dyskinesia which can be treated with a DBS electrode when traditional medical treatment fails. The neurostimulation blocks the symptoms of the disease resulting in increased quality of life for the patient. Besides this aim, one major benefit of this treatment is that the symptoms are reversible.

The electrode presently used consists of a tip with four platinum conductors and connecting wire coils embedded in silicone. The electrode is placed in the nervous tissue by a stereotaxic operation whereby the electrode tip is placed in the desired target with an accuracy of 0.5 mm. To determine the stereotaxic coordinates of the desired target, a stereotaxic frame is fixed onto the patient's head. The frame functions as an external Cartesian coordinate system with X, Y and Z axes. The next step is a computerized tomography (CT) scan or magnetic resonance imaging (MRI) resulting in CT or MR images displaying the brain anatomy and the external stereotaxic frame. From these images, the appropriate coordinate set of any brain region can now be determined. Briefly explained, the following surgery consists of a burr hole made in the patient's scull under local anesthesia. A mandrin consisting of a thin stainless steel tube, fixed onto the stereotaxic frame with a blunt tipped stilette inside is gently introduced into the brain of the patient. The tip of the mandrin is placed just above the desired target (approximately 5 mm) whereupon the stilette is removed and the quadripolar electrode is introduced through the steel tube. The electrode which is highly flexible is kept rigid by a thin inner tungsten stilette. With the electrode just above the target area, test stimulation is performed and a neurologist is simultaneously assessing the stimulation effect on the parkinsonian symptoms of the awake patient. If no effect is determined the electrode is advanced stepwise towards the target area with test stimulation and neurological assessment at each step. When the level of maximal stimulation effect is determined, the electrode is left in situ and the tungsten stilette is removed. The patient is now placed under general anesthesia and the electrode is connected through an extra conductor to the pulse generator which is usually implanted subcutaneously in the pectoral region. The system can be controlled after the implantation by telemetry.

The present technique only allows for exploration and stimulation of linear tracts of brain tissue. The placement of the electrode is therefore critical, and if the desired target is not reached in the first attempt, a second tract must be made with a statistical doubling of the surgical risk. The related art also described the use of five simultaneous tracts to carry out electro-physiological microcellular recording to determine the optimal target area followed by retracting the five microelectrodes and implanting up to five electrodes per stimulation site. The probability of surgically induced bleeding would accordingly be expected to be increased fivefold.

On the basis of the techniques known in the art, it is the object of the invention to provide an improved electrode device and an implantation method capable of providing a more accurate electro-physiological stimulation than the already existing techniques. In particular, the object is to provide a more accurate determination of the target area in the brain tissue. Furthermore, the object is to reduce the risk of side effects potentially caused by an electrical treatment with deep brain stimulation (DBS).

The invention consist of a multifunction electrode device for neural tissue stimulation, in particular for deep brain stimulation, comprising an elongated flexible electrode body having a head section that is provided with a plurality of electrode conductors with associated electrical connections imbedded in the elongated body, wherein a stilette is provided in the elongated body, said stilette comprising an insulating coating around an electrically conductoring core and an exposed microtip where said tip of the stilette can be advanced through the tip of the electrode body for the performance of microelectrode recordings.

This will allow for a more accurate determination of the desired target area than with the existing test stimulation using the electrode conductors. The procedure of electro-physiological recording and permanent electrode implantation can furthermore be made in one step if the desired target is reached.

In the preferred embodiment of the electrode device according to the invention, the stilette is made of tungsten. Moreover, the stilette is preferably provided with an electrically isolated body of plastic polymer or the like with an exposed tip, preferably 1 $\mu$m or more in diameter, and the stilette of the electrode device could be connected to a microdrive in order to allow for both intracellular and extracellular electro-physiological recordings.

The elongated electrode body is provided in an inflexible insertion tube for the insertion of the electrode device to the determined implant position. This insertion tube can be made of stainless steel or other suitable biochemically inert material. By the use of this stiff, straight cartridge tube, the electrode can be guided into place, whereafter the flexible electrode device is advanced through the tube. Subsequently, the tube is retracted and the electrode is left in its position.

In a second embodiment, the head section of the elongated body is provided with a tension bend, preferably at a length of 2–50 mm and a bending angle between 1°–179°. Hereby, the electrode is provided with a bent configuration in its resting position. The flexible electrode is inserted into place in the straight insertion tube where it is positioned in a tensioned straight configuration. As the insertion tube is retracted and the electrode device is thereby left exposed, the electrode device will take on its natural form, i.e. its bent configuration.

This embodiment of an electrode device, according to the invention, relates to the case where no or suboptimal stimulation effect is achieved in one tract. An electrode with a tension bent tip is then introduced through the steel tube of the mandrin and as the tip exits from the steel tube, it will bend at the predetermined angle in any desired 360 degree direction. By retracting the electrode into the steel tube of the mandrin, advancing it and introduction the bending electrode tip again, a cylindrical volume of nervous tissue can be examined with regard to the optimal permanent electrode placement.

The tension bend in this embodiment of the invention comprises a string of silicone, resorbable biocomposite or any other suitable inert plastic polymer denser on either the concave or convex side of the bend. Hereby, the desired tension effect can be achieved together with the required flexibility of the electrode device.

In a third embodiment of the electrode device, according to the invention, the head section comprises two or more bendable electrode legs, each tip of said bendable electrode legs being provided with an electrode conductor. Upon introduction of the electrode device, the two or more bendable legs will bend at a preferred angle out into the nervous tissue as they exit from the steel tube of the mandrin. One kind of this electrode device consists of four legs with a monoploar electrode conductor at each end. An additional electrode conductor is placed just over the bifurcation of the electrode legs. This will allow macrostimulation of a volume of nervous tissue that is tetrahedral in shape. The tension bend of each individual leg will consist of a string of silicone, resorbable biocomposite or any biologically inert plasticpolymer denser on one side than on the other that will allow this bend. Another alternative is that the legs of the electrode tip spread passively as they exit from the tip of the steel tube of the mandrin. This passive spread is achieved by a conical or paraboloidal hollow tip that will separate the legs of the electrode tip by pressure of the nervous tissue as the electrode is advanced. It is understood that this examination can be made in combination with electrophysiological microrecording through the electrode tungsten stilette/ electrode as described above under the first kind of the electrode. In the present case, the tungsten stilette with its isolated body and exposed microtip can be advanced from the tip of the tetrahedral volume and to its base. Alternatively, a stilette with a tension bent tip can be employed to better address the tetrahedral volume. This kind of electrode allows stimulation of larger brain volumes than is possible with related art electrodes.

Each of the bendable legs could preferably comprise a string of silicone, resorbable biocomposite or any other suitable biologically inert plastic polymer denser on either the concave or convex side of the bendable legs in a manner similar to the achievement of the bending in the above-mentioned second embodiment of the electrode device, according to the invention.

In a fourth embodiment, at least some of the electrode conductors are asymmetrically arranged on the head section of the electrode device, preferably in a linear configuration on one side of the electrode body. In this embodiment, the electrode device could comprise monopolar, bipolar or multipolar electrode conductors at the tip. Each electrode conductor contains oriented points of contact with the nervous tissue as opposed to the 360 degree contact of the related art electrodes. This kind of the electrode conductor creates an asymmetrical electrical field in the direction of the conductor's contact with the nervous tissue. This allows for a stimulation of the surrounding nervous structures. It is understood that electrophysiological microrecording through the electrode tungsten stilette, as described above under the first kind of the electrode, can also be used in this case. Alternatively, a tungsten stilette with a tension bent tip can be employed to better address the nervous tissue volume in the direction of the asymmetrical electrical flux field. This kind of electrode device will allow stimulation of larger brain volumes than is possible with related art electrodes.

The electrode device, according to any of the described embodiments of the invention, is preferably provided as a quadripolar electrode device.

In a second aspect of the invention, a permanent electrode implantation for neural tissue stimulation is described, in particular for deep brain stimulation, comprising an electrode device, according to the first aspect of the invention, where the electrode conductors and the stilette are electrically connected to a pulse generating device for generating an electrical stimulation field of the neural tissue at the point of implant.

The invention also provides a method of implanting a multifunction electrode device for neural tissue stimulation, in particular for deep brain stimulation according to the first aspect, wherein the electrode device is inserted for determination of the desired electrode placement by performing electro-physiological recordings through the combined stilette and microelectrode and for a permanent implantation of the electrode device once the desired target is located.

In a preferred embodiment of the method, the electrode device with a tension bent tip is introduced through the insertion tube of a mandrin and as the tip exits from the steel tube, it will bend in a predetermined angle that can be turned in any desired 360 degree direction by rotating the electrode body.

By retracting the electrode into the steel tube of the mandrin, advancing it and introducing the bending electrode tip again, a cylindrical volume of nervous tissue can be examined with regard to the optimal permanent electrode placement. Hereby, a particular advantageous method for determination of the optimal electrode placement is achieved. It is understood that this examination can be made in combination with electro-physiological micro-recording through the electrode tungsten stilette as described in the first aspect of the invention.

The advantages of an electrode device, according to the invention, are the induction of a minimal surgical trauma as only one tract in the nervous tissue over the desired target is needed in most cases. Electro-physiological micro-recording can be made in conjunction with the implantation of the permanent stimulation electrode. The second embodiment of the electrode device, according to the invention, moreover, allow a cylindrical volume of nervous tissue to be probed. Larger stimulation volumes can be reached with the third embodiment of the electrode device, according to the invention, and increased selective stimulation can be achieved with the fourth embodiment of the electrode device, according to the invention.

Figure 4:
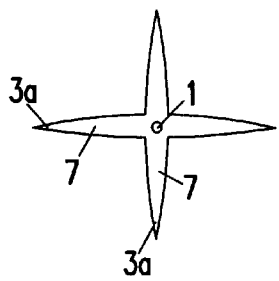
Figure 5:
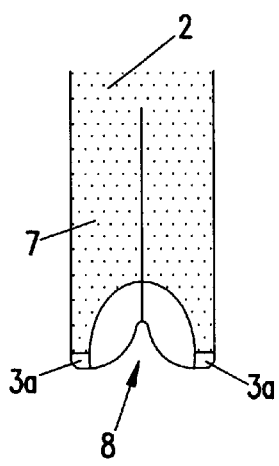
Figure 6:
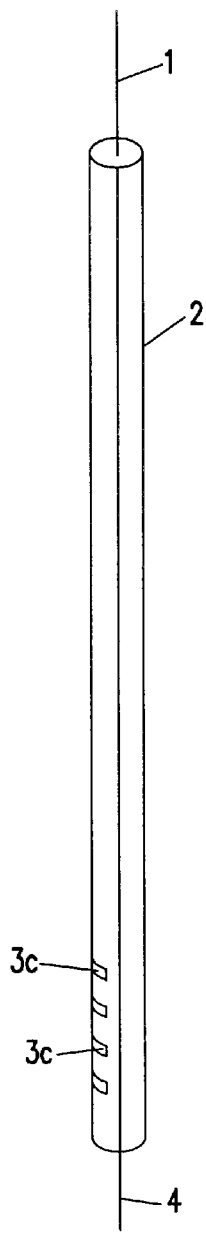

The invention will be described in detail below with reference to the accompanying drawings in which FIG. 1 is a schematic view of the head section of an electrode device according to the invention, FIG. 2 is a schematic view of the head section of an electrode device, according to the invention in a first embodiment, having a tension bent configuration, FIG. 3 is a schematic side view of the head section of a split electrode device, according to a third embodiment of the invention, FIG. 4 is an end view of the electrode in FIG. 3, FIG. 5 is a detailed cross-section view of the tip of the electrode in FIG. 3, and FIG. 6 is a schematic view of the head section of an electrode device, according to the fourth embodiment of the invention.

FIG. 1 shows a principal embodiment of an electrode device, according to the invention. The electrode device comprises a tungsten stilette 1 that is also functioning as an electrode. Said stilette 1 is shiftably mounted in a tubular configurable electrode body 2 preferably made of silicone which functions as an electrical insulation. In the tip section of the electrode body 2, four electrical electrode conductors 3 are arranged. The electrode conductors 3 are preferably platinum electrode conductors connected to a pulse generator (not shown) through internal wiring in the silicone insulation 2. The stilette 1 can be advanced through the tip of the electrode body 2. The stilette 1 comprises a tungsten electrode coated with an insulation. However, at the tip of the stilette 1, an exposed tip 4 of the electrode is provided.

The desire electrode placement is obtained by electrophysiological recordings through the combined tungsten stilette/microelectrode 1. The procedure of electrophysiological recording and permanent electrode implantation can furthermore be made in one step once the desired target is reached.

The electrode device is placed in the nervous tissue in the brain of a patient by a stereotaxic operation whereby the electrode tip is placed in the desired target with an accuracy of approx. 0.5 mm. To determine the stereotaxic coordinates of the desired target, a stereotaxic frame is fixed onto the patient's head. The frame functions as an external Cartesian coordinate system with X, Y and Z axes. The next step is a computerized tomography (CT) scan or magnetic resonance imaging (MRI) resulting in CT or MR images displaying the brain anatomy and the external stereotaxic frame. From these images, the appropriate coordinate set of any brain region can now be determined. Briefly explained, the following surgery consists of a burr hole made in the patient's scull under local anesthesia. A mandrin comprising a thin stainless steel tube, fixed onto the stereotaxic frame followed by an internal electrode device, according to the invention, is gently introduced into the brain of the patient. The tip of the mandrin is placed just above the desired target (approximately 5 mm) whereupon the stilette 1 is advanced through the tip of the quadripolar electrode introduced through the steel tube. The electrode which is highly flexible is kept rigid by a thin inner tungsten stilette. With the electrode device just above the target area, the stimulation effect is assessed e.g. on the parkinsonian symptoms of the patient. If no effect is determined the stilette/microelectrode tip 4 is advanced stepwise towards the target area with test stimulation and neurological assessment at each step. When the level of maximum stimulation effect is determined, the electrode device and the microelctrode tip 4 of the stilette 1 are left in situ.

In a second embodiment, the electrode device is provided with a tension bend 5, on which the electrode conductors 3 are arranged, as shown in FIG. 2. The tension bent configuration 5 is achieved by the use of a string of silicone, resorbable biocomposite or any other suitable inert plastic polymer denser on either the concave or convex side of the bend. The flexible electrode body 2 of silicone insulation takes on a naturally bent configuration 5, but can be straightened out when inserted in an insertion tube.

The flexible electrode device with the tension bent tip is introduced in a straight configuration through the insertion steel tube of the mandrin, and as the tip exits from the steel tube, it will bend at a predetermined angle. The electrode device and consequently the bend 5 can be turned in any desired 360 degree direction. By retracting the electrode into the steel tube of the mandrin, advancing it and introducing the bending electrode tip 5 again, a cylindrical volume of nervous tissue can be examined with regard to the optimal permanent electrode placement.

In FIGS. 3 to 5, another embodiment of the invention is shown. In this embodiment, the tip of the electrode silicone insulation 2 is provided with four bendable electrode legs 7, each carrying an electrode conductor 3a on the tip of the leg 7. Above the legs on the electrode body 2, an annular electrode conductor 3b is arranged. This will allow macrostimulation of a volume of nervous tissue that is tetrahedral in shape.

Similar to the bend 5 in the second embodiment, the tension bend of each individual leg 7 can be achieved by the use of a string of silicone, resorbable biocomposite or any biologically inert plasticpolymer denser on the concave or convex side.

Another alternative is that the legs 7 of the electrode tip spread passively as they exit from the tip of the steel tube of the mandrin. This passive spread is achieved by a conical or paraboidal hollow tip 8 that will separate the legs 7 of the electrode tip by pressure on the nervous tissue as the electrode device is advanced.

The electrode implantation can be made in combination with electro-physiological micro-recording through the electrode tungsten stilette 1. In the electrode device according to the invention, the tungsten stilette 1 with its isolated body and exposed microtip 4 can be advanced from the top center of the tetrahedral volume to its base. Alternatively, a stilette 1 with a tension bent tip can be employed to better address the tetrahedral volume.

FIG. 6 shows an electrode device containing monopolar, bipolar or multipolar electrode conductors 3c at the tip. Each electrode conductor 3c contain oriented points of contact with the nervous tissue. This kind of electrode device results in an asymmetrical electrical field in the direction of the conductor contact with the nervous tissue. A selective stimulation of the nervous tissue in the direction of the asymmetrical electrical field is achieved.

Electro-physiological microrecording through the electrode tungsten stilette 1 can be made. A tungsten stilette 1 with a tension bent tip can be employed to better address the nervous tissues volume in the direction of the asymmetrical electrical flux field.

Improved techniques whereby electrical deep brain stimulation to treat symptoms of central and peripheral nervous system disorders such as those found in e.g. Parkinson's disease, epilepsy, psychiatric illnesses and intractable pain of similar nature, the use of a quadripolar deep brain stimulation electrode connected to an implantable pulse generator have been expanded. By implantation of an electrode, it is important for the outcome to locate the optimal placement of the electrode. By the invention, an electrode device is provided that will allow stimulation of a larger volume of neural tissue in combination with simultaneous microelectrode recording. Other improvements involve a temporary electro-physiological microrecording microelectode/stilette 1, a bent electrode tip, a split electrode tip or an asymmetrical electrical stimulation field. This technique allows less traumatic localisation of the optimal neural stimulation area by microelectrode recording in combination with placement of the permanent deep brain stimulation electrode.

What is claimed is:

1. A multifunction electrode device for neural tissue stimulation, comprising an elongated flexible electrode body that comprises a head section that comprises a plurality of electrode conductors, and electrical connections associated with the electrode conductors embedded in the elongated body, further comprising a stilette disposed within the elongated body, said stilette comprising an insulating coating around an electrically conducting core and an exposed tip, said tip of the stilette being advanceable through a tip of the electrode body for the performance of electrode recordings, the head section of the elongated body comprising a tension bend.

2. A multifunction electrode device according to claim 1, wherein the stilette comprises tungsten.

3. A multifunction electrode device according to claim 1, wherein the stilette comprises an electrically isolated body of plastic polymer comprising an exposed tip, the exposed tip being 1 $\mu$m ore more in diameter.

4. A multifunction electrode device according to claim 1, wherein the stilette of the electrode device is in communication with a microdrive so as to enable intracellular and extracelluar electrophysiological recordings.

5. A multifunction electrode device according to claim 1, wherein the elongated electrode body is moveably disposed within an inflexible insertion tube for insertion of the electrode device to a determined implant position.

6. A multifunction electrode device according to claim 5, wherein the electrode device is rotatable within the insertion tube, and wherein the device further comprises indications means in communication with at least one of the electrode device and the insertion tube for registration of a relative angular position relative angular position of the electrode device and the insertion tube.

7. A multifunction electrode device according to claim 1, wherein the tension bend has a length of 2–50 mm and a bending angle between 1° and 179°.

8. A multifunction electrode device according to claim 7, wherein the tension bend comprises a string of inert plastic polymer denser on one of the concave and convex sides of the bend.

9. A multifunction electrode device according to claim 1, wherein the head section comprises two or more bendable electrode legs having tips, and wherein each tip of said bendable electrode leg comprises an electrode conductor.

10. A multifunction electrode device according to claim 9, further comprising a conductor just above a bifurcation of the electrode legs.

11. A multifunction electrode device according to claim 9, wherein each of the bendable legs comprises a string of inert plastic polymer denser on one of the concave and convex sides of the bendable legs.

12. A multifunction electrode device according to claim 9, wherein the electrode conductor comprises a hollow tip having a shape of one of the group consisting of conical and paraboidal, and wherein the outermost section of the stilette is provided with means for spreading said bendable legs as the stilette is advanced outwards.

13. A multifunction electrode device according to claim 1, wherein at least some of the electrode conductors are asymmetrically arranged on the head section of the electrode device.

14. A multifunction electrode device according to claim 1, wherein the electrode device is a quadripolar electrode device.

15. A multifunction electrode device according to claim 7, wherein the string of inert plastic polymer denser comprises at least one of the group consisting of silicon and resorbable biocomposite.

16. A multifunction electrode device according to claim 11, wherein the string of inert plastic polymer denser on the legs comprises at least one of the group consisting of silicone and resorbable biocomposite.

17. A multifunction electrode device according to claim 13, wherein at least some of the electrode conductors are arranged in a linear configuration on one side of the electrode body.

18. A permanent electrode implantation for neural tissue stimulation comprising an electrode device, the electrode device comprising an elongated flexible electrode body that comprises a head section that comprises a plurality of electrode conductors, and electrical connections associated with the electrode conductors embedded in the elongated body, further comprising a stilette disposed within the elongated body, said stilette comprising an insulating coating around an electrically conducting core and an exposed tip, said tip of the stilette being advanceable through a tip of the electrode body for the performance of electrode recordings, the head section of the elongated body comprising a tension bend, wherein the electrode conductors and the stilette are electrically connected to an implantable pulse generating device for generating an electrical stimulation field of the neural tissue at a point of implant.

19. A method of implantation of a multifunction electrode device for neural tissue stimulation, the electrode device comprising an elongated flexible electrode body that comprises a head section that comprises a plurality of electrode conductors, and electrical connections associated with the electrode conductors embedded in the elongated body, further comprising a stilette disposed within the elongated body, said stilette comprising an insulating coating around an electrically conducting core and an exposed tip, said tip of the stilette being advanceable through a tip of the electrode body for the performance of electrode recordings, the head section of the elongated body comprising a tension bend, the method comprising the steps of inserting the electrode device to determine a desired electrode target by performing electro-physiological recordings through the combined stilette and electrode, and permanently implanting the electrode device once the desired target is located.

20. A method according to claim 19, further comprising the step of introducing the electrode device through an insertion tube of a mandrin such that as the tip exits from the insertion tube it bends at a predetermined angle, and such that the bent tip is rotatable through 360 degrees by rotating the electrode body.

21. A method according to claim 19, further comprising the steps of determining an optimal permanent electrode placement for the electrode device by retracting the electrode device into the insertion tube of the mandrin, adjusting its angular position relative to the insertion tube by rotation and advancing the electrode device through the tube, repeatedly introducing the bending electrode tip throughout a section of a cylindrical volume of nervous tissue and examining a result thereof to determine an optimal permanent electrode placement.

\* \* \* \* \*